US011952455B2

(12) United States Patent
Kubo et al.

(10) Patent No.: US 11,952,455 B2
(45) Date of Patent: Apr. 9, 2024

(54) FOAM AND COMPOSITION FOR FOAM

(71) Applicant: ALCARE CO., LTD., Tokyo (JP)

(72) Inventors: Takabumi Kubo, Tokyo (JP); Tomoya Tanaka, Tokyo (JP); Ryota Watanabe, Tokyo (JP)

(73) Assignee: ALCARE CO., LTD., Tokyo (JP)

( * ) Notice: Subject to any disclaimer, the term of this patent is extended or adjusted under 35 U.S.C. 154(b) by 99 days.

(21) Appl. No.: 16/474,865

(22) PCT Filed: Dec. 28, 2017

(86) PCT No.: PCT/JP2017/047376
§ 371 (c)(1),
(2) Date: Jun. 28, 2019

(87) PCT Pub. No.: WO2018/124303
PCT Pub. Date: Jul. 5, 2018

(65) Prior Publication Data
US 2019/0322795 A1 Oct. 24, 2019

(30) Foreign Application Priority Data
Dec. 29, 2016 (JP) .................. 2016-258014

(51) Int. Cl.
*A61L 15/26* (2006.01)
*A61L 15/42* (2006.01)
*A61L 27/26* (2006.01)
*A61L 27/56* (2006.01)
*A61L 28/00* (2006.01)
*C08G 18/00* (2006.01)
*C08G 18/08* (2006.01)
*C08G 18/42* (2006.01)
*C08G 18/48* (2006.01)
*C08G 18/73* (2006.01)
*C08G 18/76* (2006.01)
*C08L 1/06* (2006.01)
*C08L 1/28* (2006.01)
*C08L 5/06* (2006.01)
*C08L 75/04* (2006.01)

(52) U.S. Cl.
CPC .............. *C08G 18/76* (2013.01); *A61L 15/26* (2013.01); *A61L 15/425* (2013.01); *A61L 27/26* (2013.01); *A61L 27/56* (2013.01); *A61L 28/0015* (2013.01); *A61L 28/0053* (2013.01); *C08G 18/14* (2013.01); *C08G 18/42* (2013.01); *C08G 18/48* (2013.01); *C08G 18/73* (2013.01); *C08L 1/286* (2013.01); *C08L 5/06* (2013.01)

(58) Field of Classification Search
CPC ...... A61L 15/16; C08G 18/14; C08G 18/6484
See application file for complete search history.

(56) References Cited

U.S. PATENT DOCUMENTS

| RE31,757 E | * | 12/1984 | Kennedy | ............ C08G 18/6484 521/103 |
| 5,064,653 A | | 11/1991 | Sessions et al. | |
| 5,336,695 A | * | 8/1994 | Nass | .............. C08L 75/08 521/905 |
| 5,844,013 A | * | 12/1998 | Kenndoff | ............... C08G 18/08 521/137 |
| 6,566,576 B1 | | 5/2003 | Komerska et al. | |
| 8,673,992 B2 | | 3/2014 | Eckstein et al. | |
| 2004/0153040 A1 | | 8/2004 | Martineau et al. | |
| 2007/0179210 A1 | | 8/2007 | Swaniker | |
| 2014/0330235 A1 | | 11/2014 | Swaniker | |
| 2015/0329665 A1 | | 11/2015 | Pernot | |

FOREIGN PATENT DOCUMENTS

| GB | 2111425 A | * | 7/1983 | ............. C04B 35/66 |
| GB | 2277031 A | * | 10/1994 | |
| JP | H02-43231 A | | 2/1990 | |
| JP | 2000-175958 A | | 6/2000 | |
| JP | 2008524410 A | * | 10/2008 | |
| JP | 2009-525389 A | | 7/2009 | |
| JP | 2012-506460 A | | 3/2012 | |
| JP | 2016-504454 A | | 2/2016 | |
| WO | 2008/157711 A2 | | 12/2008 | |
| WO | 2008-157711 A2 | | 12/2008 | |

OTHER PUBLICATIONS

Extended European Search Report mailed by European Patent Office dated Aug. 7, 2020 in corresponding European patent application No. 17888904.4-1102.
International Search Report issued for corresponding PCT/JP2017/047376 application.
European Office Action mailed by European Patent Office dated Aug. 12, 2021 in corresponding European patent application No. 17 888 904.4.
Chinese Office Action mailed by Chinese Patent Office dated Jul. 22, 2021 in corresponding Chinese patent application No. 201780080562.3.
Japanese Office Action mailed by Japanese Patent Office dated Aug. 10, 2021 in corresponding Japanese patent application No. 2018-559648.
Chinese Office Action mailed by Chinese Patent Office dated Feb. 14, 2022, in corresponding Chinese patent application No. 201780080562.3.
Japanese Office Action mailed by Japanese Patent Office dated Apr. 19, 2022, in corresponding Japanese patent application No. 2018-559648.

(Continued)

*Primary Examiner* — Melissa A Rioja
(74) *Attorney, Agent, or Firm* — IP Business Solutions, LLC

(57) ABSTRACT

The present invention provides a foam having a surface which solates or gelates after absorption of water and appropriately absorbs the water. The foam is prepared by a foam reaction of a mixture comprising at least one polyol, a compound having at least one isocyanate group, and a hydrophilic polymer.

16 Claims, 3 Drawing Sheets

(56) References Cited

OTHER PUBLICATIONS

Japanese Office Action mailed by Japanese Patent Office dated Oct. 11, 2022, in corresponding Japanese patent application No. 2018-559648.
Chinese Office Action mailed by Chinese Patent Office dated Jun. 17, 2022, in corresponding Chinese patent application No. 201780080562.3.
Extended European Search Report mailed by European Patent Office dated Feb. 22, 2023 in corresponding European patent application No. 17 888 904.4-1102.

* cited by examiner

FOAM AND COMPOSITION FOR FOAM

TECHNICAL FIELD

The present invention relates to foams and compositions for foams.

BACKGROUND ART

Foams are used in applications to a variety of products to be in contact with skin.

Wound dressings are used in treatment of wounds in general and surgical wounds. The wound dressings basically have a function to physically protect wounded surfaces to prevent external infection. There are a variety of wound dressings, which are appropriately selected according to the state of the wound or the purpose of the treatment in use.

An example of the wound dressings is a so-called hydrocolloid material comprising a flexible hydrophobic polymer and a hydrophilic polymer dispersed therein. The hydrophilic polymer in the hydrocolloid material absorbs exudates from the wounded surface to solate or gelate. This solated or gelated polymer is believed to keep a wet environment of the wounded surface to promote the cure of the wound and provide pain relief. The hydrocolloid material is also used as a tackifier for skin in colostomy devices.

Another example of the wound dressings is a so-called polyurethane foam composite comprising a resin foam (for example, Patent Literature 1). Hereinafter, the polyurethane foam composite may also be simply referred to as a foam composite or foam. The foam composite is a porous material made of polyurethane. After the foam is applied to the wounded surfaces, its pores absorb the exudate.

CITATION LIST

Patent Literature

Patent Literature 1: Japanese Unexamined Patent Application Publication No. 2000-175958

SUMMARY OF INVENTION

Technical Problem

Traditional methods have difficulties in production of a foam composite having a surface which solates after absorption of water on the skin surface as the hydrocolloid material does, and appropriately absorbs the water as the polyurethane foam material does.

An object of the present invention is to provide a foam having a surface which solates or gelates after absorption of water and appropriately absorbs the water.

Solution to Problem

To solve the problem above, the present invention provides a foam prepared by a foam reaction of a mixture comprising at least one polyol, a compound having at least one isocyanate group, and a hydrophilic polymer.

Advantageous Effect of Invention

The foam according to the present invention provides a wound dressing having a surface to be applied to a wound, the surface solating and appropriately absorbing an exudate during application of the wound dressing to the wound. The foam can also provide a member for a colostomy device and artificial bladder which member is suitable for patients who sweat a lot.

DESCRIPTION OF EMBODIMENTS

Suitable embodiments for implementing the present invention will now be described. The following description provides representative embodiments of the present invention, and should not be construed as limitation to the scope of the present invention.

Figure 1:
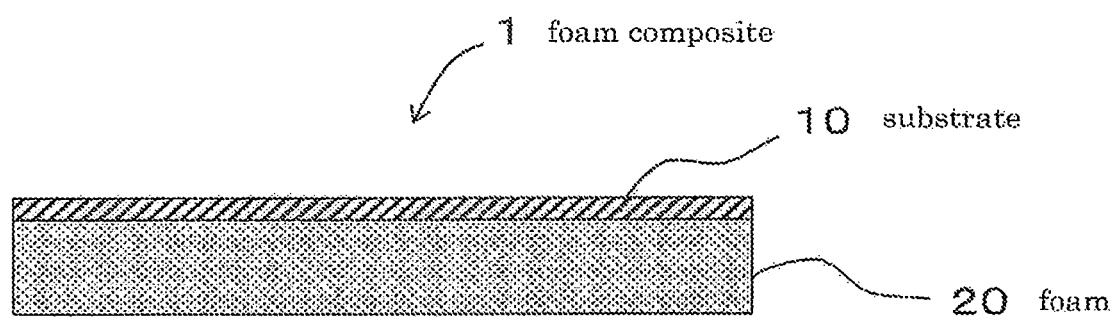
FIG. 1 is a sectional schematic view of a foam composite including a foam according to the present invention.
Figure 2:
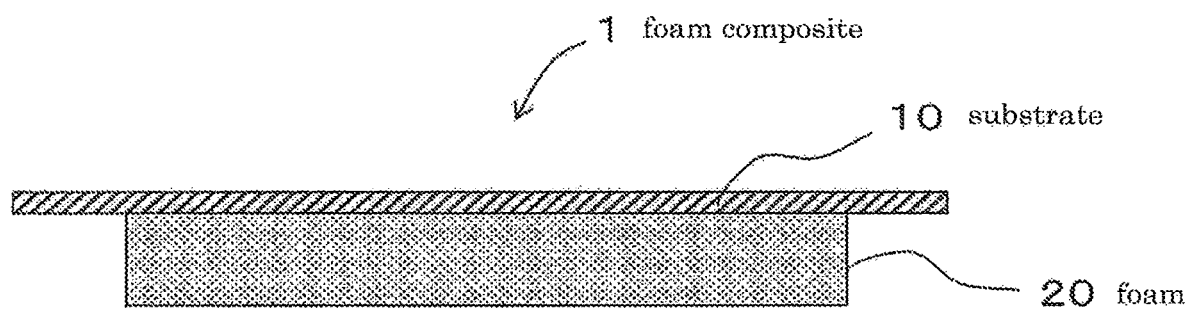
FIG. 2 is a sectional schematic view of a foam composite including a foam according to the present invention.

A foam composite will now be described as an application of the foam according to the present invention with reference to FIGS. 1 and 2. FIG. 1 is a sectional view of the foam composite according to one embodiment of the present invention.

An exemplary foam composite 1 used for protection and treatment of wounds includes a foam 20 and a substrate 10. The foam composite may also consist only of the foam with no substrate. Alternatively, as illustrated in FIG. 2, the substrate may have a size such that the substrate protrudes from the foam. In this case, a tackifier may be applied to the protrusion of the substrate to enhance the adhesive force of the foam composite to a surface of a body. The substrate 10 to be used may be composed of a waterproof water-permeable film, such as a polyurethane film or a polyester film. The substrate 10 may be integrated with the foam 20 with an adhesive applied to a surface of the substrate 10. The foam according to the present invention may also be used alone as a foam composite.

In another embodiment, the foam according to the present invention may also be used as a skin protector, for example, a member of a faceplate for a colostomy device or artificial bladder (hereinafter, also referred to as ostomy appliance in some cases). The foam composite used as a member of the faceplate for ostomy appliances may also be produced with a composition and by a method suitable for the following applications. The foam according to the present invention may also be used in wound dressings, skin protectors for ostomy appliances, skin tapes for fixation and/or protection, and materials for hemostasis (hemostatic materials). The foam according to the present invention used in wound dressings, skin protectors for ostomy appliances, skin tapes for fixation and/or protection, or materials for hemostasis (hemostatic materials) may also have a suitable composition described below and may be prepared by a suitable method described below.

The materials used in preparation of the foam according to the present invention will now be described.

(Urethane)

The foam according to the present invention comprises a urethane resin prepared by expansion of a mixture of at least one polyol, a compound having at least one isocyanate group, and a hydrophilic polymer. A blowing agent is preferably compounded for efficient foaming. In the present invention, as described later, it is preferred that at least one polyol be reacted with a compound having at least one isocyanate group in the presence of a hydrophilic polymer containing a blowing agent. It is preferred that the at least one polyol and the compound having at least one isocyanate group be solvent-free in production of a homogeneous foam. For the relation between the OH equivalent of the polyol and the NCO equivalent of the compound having at least one isocyanate group in the foam according to the present invention, the ratio NCO/OH may be any value. The ratio is preferably 0.5 or more and 0.9 or less. The OH equivalent of the polyol is preferably 1000 or more and the NCO equivalent of polyisocyanate is preferably 100 or more.

(Polyol)

The foam according to the present invention can be prepared with a polyol for polyurethane foams. Any commercially available polyol can be used without limitation. Preferred are polyols for medical products to enhance the safety when the foam according to the present invention material is applied to human bodies.

The polyol is compounded in an amount of preferably 25 to 80 mass %, more preferably 50 to 70 mass % of the total mass of the mixture of materials before foaming.

Examples of the polyol include polyether polyols, polyester polyols, or polycarbonate polyols. Examples of the polyether polyol include polypropylene ether glycol and polytetramethylene glycol. Examples of the polyester polyol include polybutylene adipate and polycaprolactone glycol. Examples of the polycarbonate polyol include 1,6-hexane polycarbonate diol. Although these compounds are usually used alone, these compounds may also be used in combination.

(Compound Having at Least One Isocyanate Group)

The foam according to the present invention can be prepared with a compound having at least one isocyanate group (hereinafter, referred to as an abbreviation "isocyanate" in some cases) for polyurethane foams. Any commercially available isocyanate can be used without limitation. Preferred are isocyanates for medical products to enhance the safety when the foam according to the present invention material is applied to human bodies.

In general, the isocyanates for preparing a urethane foam are categorized into aromatic, alicyclic, and aliphatic isocyanates. Any one of these isocyanates that can have an appropriate expansion rate and appropriate characteristics as a foam composite may be used. The isocyanate may have several isocyanate groups in one molecule. The isocyanate may be a prepolymer prepared through preliminary polymerization of a monomer having several isocyanate groups.

Examples of the compound having at least one isocyanate group include aromatic diisocyanates, such as 4,4'-diphenylmethane diisocyanate, m- and p-phenylene diisocyanates, and 2,4- and 2,6-tolylene diisocyanates; alicyclic diisocyanates, such as isophorone diisocyanate, 4-4'-dicyclohexylmethane diisocyanate, and 1,4-cyclohexylene diisocyanate; and aliphatic diisocyanates, such as hexamethylene diisocyanate. Although these compounds are usually used alone, these compounds may also be used in combination.

Examples of the usable aliphatic polyisocyanates include hexamethylene diisocyanate (HDI), lysine diisocyanate (LDI), butene diisocyanate (BDI), 1,3-butadiene 1,4-diisocyanate, octamethylene diisocyanate, and modified products thereof. Examples of the usable alicyclic polyisocyanates include isophorone diisocyanate (IPDI), dicyclohexylmethane diisocyanate [hydrogenated diphenylmethane diisocyanate (hydrogenated MDI)], hydrogenated xylene diisocyanate (hydrogenated XDI), cyclohexane diisocyanate, methylcyclohexane diisocyanate, and dicyclohexylmethane diisocyanate.

Examples of the usable polyisocyanates other than the aliphatic or alicyclic polyisocyanates include tri- or higher functional polyisocyanates, such as lysine ester triisocyanate, 1,8-diisocyanate-4-isocyanate methyloctane, 1,6,11-undecane triisocyanate, 1,3,6-hexamethylene triisocyanate, and bicycloheptane triisocyanate. Among these polyisocyanates, preferred are lysine ester triisocyanate and 1,3,6-hexamethylene triisocyanate. These polyisocyanates can be used in combination with the diisocyanates listed above. The amount thereof is preferably 60 mass % or less in the polyisocyanates.

A preferred isocyanate for preparing the foam according to the present invention is a polyisocyanate prepolymer prepared through preliminary polymerization of an aliphatic isocyanate monomer and having terminal isocyanate groups.

The amount of the compounded isocyanate is preferably 5 to 30 mass %, more preferably 8 to 30 mass % of the total mass of the mixture of materials before foaming.

(Blowing Agent)

A blowing agent is used to achieve appropriate foaming during the preparation of the foam according to the present invention. The blowing agent to be used can be water or an organic solvent.

In the case that the blowing agent is water, it is preferred that the water be absorbed by a hydrophilic polymer (described later) and then be mixed with polyol and isocyanate. In this case, the water naturally contained in the hydrophilic polymer can also be used. Heating of the mixture results in a suitable porous foam having the hydrophilic polymer dispersed therein according to the present invention. In the case that the polyol reacts with the isocyanate to form crosslinks in the presence of water as the blowing agent, the isocyanate usually reacts with water in preference to the crosslinking reaction. In the present invention, the water contained in the hydrophilic component ensures compatibility with the crosslinking reaction and generation of a foam due to the reaction of water.

Preferred organic solvents are those which are not left after foaming. Examples of the usable organic solvent include ethanol, ethyl acetate, hexane, pentane, acetone, and dichloromethane.

(Hydrophilic Polymer)

One of the features on the foam according to the present invention is that the foam contains the hydrophilic polymer. In the foam containing the hydrophilic polymer, the hydrophilic polymer absorbs exudates when the foam composite is applied to the wounded surface. Even if the foam composite applied to the wounded surface is pressed or expanded after absorption of the water, the exudate does not return to the wounded surface.

For example, if the hydrophilic polymer has a powder or fibrous form, the surface of the foam composite in contact with the wounded surface solates after the foam according to the present invention absorbs the water such as the exudate. It is said that the sol not only physically protects the wounded surface, but also contributes to pain relief.

The amount of the compounded hydrophilic polymer is preferably 5 to 50 mass %, more preferably 10 to 30 mass % of the total mass of the mixture of materials before foaming.

Although the hydrophilic polymer contains water in any amount, the amount is preferably 10 mass % or more in viewpoint of the expansion rate. According to this preferred embodiment, the foam according to the present invention has predetermined tackiness. The hydrophilic polymer may be swellable, may be water-soluble, may be swellable and water-insoluble, may be nonswellable and water-soluble, or may be nonswellable and water-insoluble. The foam according to the present invention preferably contains at least one water-soluble hydrophilic polymer. The foam according to the present invention more preferably contains at least two hydrophilic polymers, and particularly preferably contains at least one water-soluble hydrophilic polymer and at least one swellable hydrophilic polymer among the at least two hydrophilic polymers. If both the water-soluble hydrophilic polymer and the swellable hydrophilic polymer are contained, the hydrophilic polymer can turn to a solated substance on the surface of the foam and the swellable polymer can hold water. For this reason, the foam can be formed through vaporization of water during heating while the inhibition of crosslinking of the isocyanate by water can be reduced. The hydrophilic polymer according to the present invention preferably solates after water absorption, more preferably solates after water absorption in the foam and flows from the foam.

Any hydrophilic polymer, i.e., natural, semi-synthetic, or synthetic hydrophilic polymers can be used. The "semi-synthetic" is also referred to as partial chemical synthesis, which indicates chemical synthesis using compounds isolated from natural resources such as plant materials, microorganisms, or cell culture products as starting materials.

Examples of the natural hydrophilic polymers include plant-derived polymers, such as gum arabic, tragacanth gum, galactan, guar gum, carob gum, karaya gum, carrageenan, pectin, agar, and starches (such as rice, corn, potato, and wheat starches); microorganism-derived polymers, such as xanthan gum, dextrin, dextran, succionoglucan, mannan, locust bean gum, and pullulan; and animal-derived polymers, such as casein, albumin, and gelatin. Preferred pectin is citrus pectin.

Examples of the semi-synthetic hydrophilic polymers include starch polymers (such as carboxymethyl starch and methylhydroxypropyl starch); cellulose polymers (such as methyl cellulose, ethyl cellulose, methylhydroxypropyl cellulose, hydroxyethyl cellulose, sodium cellulose sulfate, hydroxypropyl cellulose, carboxymethyl cellulose, and sodium carboxymethyl cellulose); and alginate polymers (such as sodium alginate, calcium alginate, and propylene glycol alginate).

Examples of the synthetic hydrophilic polymers include vinyl polymers (such as poly(vinyl alcohol), poly(vinyl methyl ether), polyvinylpyrrolidone, and carboxyvinyl polymer); acrylic polymers (such as poly(sodium acrylate) and polyacrylamide); and polyethyleneimine.

These hydrophilic polymers may be used alone or in combination.

Among these hydrophilic polymers, preferred are one or more polymers selected from the group consisting of sodium carboxymethyl cellulose, pectin, karaya gum, mannan, guar gum, locust bean gum, and gelatin.

If an alginate polymer is used among these hydrophilic polymers, the foam according to the present invention may have hemostatic action on the wounded surface in some cases.

(Catalyst)

Use of a catalyst is preferred to efficiently react the polyol according to the present invention with the isocyanate. Any catalyst which can be used in the polyurethane foam may be used. Examples thereof include amine catalysts, such as triethylamine, triethylenediamine, diethanolamine, dimethylaminomorpholine, N-ethylmorpholine, and tetramethylguanidine; tin catalysts, such as stannous octoate and dibutyltin dilaurate; and metal catalysts, such as phenylmercury propionate, lead octenate, and zinc carbonate.

(Others)

The foam according to the present invention can contain other components mixed with the hydrophilic polymer. For example, a silver compound may be contained to impart antibacterial characteristics. A component of a bioactive substance such as sphingolipid (such as ceramide), hyaluronic acid, and astaxanthin may be contained to improve the water absorbing characteristics. A compound having buffer action, such as sodium citrate, anhydrous, can also be contained as a pH adjuster. Although the foam according to the present invention may contain a surfactant, it is preferred that the foam do not contain any surfactant. The foam according to the present invention can absorb water even without any surfactant. The surfactant-free foam according to the present invention can further reduce stimuli to the skin.

(Substrate)

The foam according to the present invention may include a substrate. The substrate to be used may be a commercially available resin film.

Examples of the resin film include polyurethanes; polyesters, such as poly(ethylene terephthalate) and poly(butylene terephthalate); polyamides, such as nylon 6 and nylon 66; polyolefins, such as polypropylene, polyethylene, low density polyethylene, high density polyethylene, and polypropylene; olefin copolymers, such as ethylene-vinyl acetate copolymers (EVA), ethylene-ethyl acrylate copolymers (EEA), ethylene-methyl acrylate copolymers (EMA), ethylene-methyl methacrylate copolymers (EMMA), ethylene-methacrylate polymers (EMAA), ethylene-acrylate copolymers (EAA); poly(vinyl alcohol); poly(vinyl chloride) and poly(vinylidene chloride); and silicones. These resins may be used alone or in combination (Preparation of Foam)

The foam according to the present invention can be prepared by mixing at least a polyol, an isocyanate, and a hydrophilic polymer, and foaming the mixture by a known method. In the foam according to the present invention, the mixture can be foamed at any timing. Preferably, the mixture is foamed within a mold for a product to reduce the number of steps. The hydrophilic polymer may be preliminarily mixed, and may be used as a hydrophilic filler.

Absorption of water, such as the exudate, by the foam according to the present invention results in the solation of the surface of the foam. This solation occurs because the hydrophilic polymer contained in the foam absorbs the water.

Unlike traditional foams, the foam according to the present invention barely releases the absorbed water. Specifically, the absorbed water is barely released even if the foam is compressed after the absorption of the water. It is believed that such an effect of the foam is achieved because the water is not only held by the pores of the foam, but also partially absorbed by the hydrophilic polymer.

In this specification, the proportion of the water released by compression of the foam to the water absorbed by the foam is defined as "water release rate". The method of calculating the water release rate will be described later.

The foam according to the present invention has a water release rate of preferably 0 to 30%, more preferably 0 to 20%.

The foam according to the present invention may have any water absorption rate. The water absorption rate after the foam according to the present invention is immersed in water for six hours is preferably 40% or more, and that after the foam is immersed in water for 24 hours is preferably 70% or more.

The foam according to the present invention may have any expansion rate. To control such that the foam has a predetermined tackiness, the expansion rate is preferably 110% to 500%, more preferably 140% to 500%.

The surfaces of the foam according to the present invention preferably have tackiness before and/or after absorption of water. The surface of the foam according to the present invention to be in contact with the surface of the body such as a wound or skin preferably has tackiness. Although the foam according to the present invention may have any tackiness, the tackiness is preferably 0.1 N or more, more preferably 0.4 N or more, still more preferably 0.4 N to 2.3 N. Preferably, the surface of the foam according to the present invention to be in contact with the surface of the body such as a wound or skin also has tackiness after water absorption. The foam according to the present invention may have any tackiness after water absorption unless it unsticks from the skin, for example. The tackiness retention rate ((tackiness of foam after water absorption)/(tackiness of foam before water absorption)) is preferably 30% or more and 250% or less. The tackiness retention rate ((tackiness of foam after water absorption)/(tackiness of foam before water absorption)) is determined through measurement of the tackiness of the foam before water absorption and that after water absorption. The foam before water absorption is a foam dried at 37° C. for 2.5 hours, for example, and the foam after water absorption is the foam that has been immersed in saline at 37° C. for 2.5 hours, for example.

The foam according to the present invention has flexibility. A greater OH equivalent of the polyol and a greater NCO equivalent of the compound having at least one isocyanate group cause an increase in flexibility in the resulting foam. Such a foam according to the present invention having flexibility readily follows and cures a wound if it is used as a wound dressing, or readily fits the skin to reduce the leakage of urine or feces if it is used as a skin protector. Although the foam according to the present invention may have any thickness, a preferred thickness is 1.5 mm or more.

(Composition for Foam)

The composition for a foam according to the present invention comprises at least one polyol, a compound having at least one isocyanate group, and a hydrophilic polymer. The contents of the at least one polyol, the compound having at least one isocyanate group, and the hydrophilic polymer are as described above, and details thereof are omitted in this section.

The amount of the compounded polyol is preferably 25 to 80 mass %, more preferably 50 to 70 mass % of the total mass of the composition for a foam. The amount of the compound having at least one isocyanate group is preferably 5 to 30 mass %, more preferably 8 to 30 mass % of the total mass of the composition for a foam. The amount of the compounded hydrophilic polymer is preferably 5 to 50 mass %, more preferably 10 to 30 mass % of the total mass of the composition for a foam.

Although the hydrophilic polymer contains any amount of water, the amount is preferably 10 mass % or more, more preferably 14 mass % or more in viewpoint of the expansion rate. The hydrophilic polymer according to the present invention is preferably water-soluble and solates after water absorption, and more preferably solates after water absorption in the foam and flows from the foam. The foam according to the present invention comprises at least two hydrophilic polymers, and preferably contains at least one water-soluble hydrophilic polymer and at least one swellable hydrophilic polymer among the at least two hydrophilic polymers. If the water-soluble hydrophilic polymer and the swellable hydrophilic polymer are contained, the hydrophilic polymer can turn to a solated substance on the surface of the foam and the swellable polymer can hold water. Thus, the foam can be formed through vaporization of water during heating while the inhibition of crosslinking of the isocyanate by water is reduced.

Although the composition for a foam according to the present invention may contain a surfactant, it is preferred that the composition do not contain any surfactant. The foam according to the present invention can absorb water even if it contains no surfactant.

EXAMPLES

The foam according to the present invention will now be described in more detail by way of Examples. Examples described below are illustrated as representative examples of the foam according to the present invention. These should not be construed as limitations to the scope of the foam according to the present invention.

A hydrophilic filler having a composition shown in Table 1 was used in Examples 1 and 2 and 5 to 9.

TABLE 1

| Names of components | Proportion (mass %) |
|---|---|
| Sodium carboxymethyl cellulose | 36.5 |
| Citrus pectin | 41 |
| Gelatin | 20 |
| Zinc oxide | 1 |
| Silver sulfadiazine | 0.5 |
| Ceramide 2 | 1 |
| Total | 100 |

Example 1

Polyol 1 (equivalent: 1320.00, 66.9 mass %), Polyisocyanate (equivalent: 203.88, 11.1 mass %), a metal carbonate catalyst (zinc) (2.0 mass %), and the hydrophilic filler (20.0%) were mixed. The mixture was heated in an oven at 105° C. to 130° C. for about 15 minutes to prepare a foam. The expansion rate was 183%. The expansion rate was measured as follows: A test sample foam formed into a sheet was punched into a diameter of 30 mm, and the thickness (A) was measured with a thickness gauge. The weight (G) was measured with a precision balance to calculate the expansion rate from the following expression:

$$\text{Expansion rate} = 1.5 \text{ cm} \times 1.5 \text{ cm} \times \pi \times A(\text{cm})/(G \div 1.1 \text{ g/cm}^3)$$

The expansion rates of the foams prepared in Examples 2 to 29 were also measured by the same method.

Example 2

A foam was prepared with the same composition and as in Example 1 except that 69.2 mass % Polyol 1, 13.8 mass % Polyisocyanate 1, and 15.0 mass % hydrophilic filler were used. The expansion rate was 281%.

Example 3

A foam was prepared as in Example 1 except that 29.1 mass % Polyol 2 (equivalent: 1602.86), 19.4 mass % Polyisocyanate 2 (equivalent: 328.13), and 1.5 mass % metal carbonate catalyst (zinc) were used, and the hydrophilic filler in Table 1 was replaced with 50.0 mass % calcium alginate. The expansion rate was 441%.

Example 4

A foam was prepared as in Example 1 except that 64.9 mass % Polyol 2, 8.7 mass % Polyisocyanate 2, and 1.5 mass % metal carbonate catalyst (zinc) were used, and the hydrophilic filler in Table 1 was replaced with 25.0 mass % calcium alginate. The expansion rate was 166%.

Example 5

Polyol 2 (equivalent: 1602.86, 61.8 mass %), Polyisocyanate (equivalent: 328.13, 12.4 mass %), a metal carbonate catalyst (zinc) (0.9 mass %), and the hydrophilic filler (25.0%) were mixed to prepare a mixture. The mixture was placed onto a polyester releasing film. The polyester releasing film with the mixture was then heated in an oven at about 110° C. for about one hour, and was further heated at about 40° C. for about three days to prepare a foam. The expansion rate was 422%.

Example 6

A foam was prepared as in Example 5 except that 64.0 mass % Polyol 2, 8.0 mass % polyisocyanate 2, 3.0 mass % metal carbonate catalyst (zinc), and 25.0 mass % hydrophilic filler were used. The expansion rate was 134%.

Example 7

A foam was prepared as in Example 5 except that 62.6 mass % Polyol 2, 10.4 mass % Polyisocyanate 2, 2.0 mass % metal carbonate catalyst (zinc), and 25.0 mass % hydrophilic filler were used. The expansion rate was 253%.

Example 8

A foam was prepared as in Example 5 except that 61.40 mass % Polyol 2, 12.30 mass % Polyisocyanate 2, 1.50 mass % metal carbonate catalyst (zinc), and 25.00 mass % hydrophilic filler were used. The expansion rate was 314%.

Example 9

A foam was prepared as in Example 5 except that 61.40 mass % Polyol 2, 12.30 mass % Polyisocyanate 2, 1.50 mass % metal carbonate catalyst (zinc), and 25.00 mass % dried hydrophilic filler were used. The expansion rate was 112%.

Example 10

A foam was prepared as in Example 5 except that 60.08 mass % Polyol 2, 14.72 mass % Polyisocyanate 2, and 0.20 mass % bismuth-based catalyst were used, and the hydrophilic filler in Table 1 was replaced with 25.00 mass % sodium carboxymethyl cellulose (CMCNa). The expansion rate was 206%.

Example 11

A foam was prepared as in Example 5 except that 70.54 mass % Polyol 3 (equivalent: 2077.78), 14.26 mass % Polyisocyanate 3 (equivalent: 700.00), and 0.20 mass % bismuth-based catalyst were used, and the hydrophilic filler in Table 1 was replaced with 15.00 mass % sodium carboxymethyl cellulose (CMCNa). The expansion rate was 119%.

Example 12

A foam was prepared as in Example 5 except that 72.66 mass % Polyol 3, 17.14 mass % Polyisocyanate 3, and 0.20 mass % bismuth-based catalyst were used, and the hydrophilic filler in Table 1 was replaced with 10.00 mass % sodium carboxymethyl cellulose (CMCNa). The expansion rate was 102%.

Example 13

A foam was prepared as in Example 5 except that 56.48 mass % Polyol 3, 13.32 mass % Polyisocyanate 3, and 0.20 mass % bismuth-based catalyst were used, and the hydrophilic filler in Table 1 was replaced with 30.00 mass % sodium carboxymethyl cellulose (CMCNa). The expansion rate was 154%.

Example 14

A foam was prepared as in Example 5 except that 70.73 mass % Polyol 3, 19.07 mass % Polyisocyanate 3, and 0.20 mass % bismuth-based catalyst were used, and the hydrophilic filler in Table 1 was replaced with 10.00 mass % sodium carboxymethyl cellulose (CMCNa). The expansion rate was 125%.

Example 15

A foam was prepared as in Example 5 except that 68.60 mass % Polyol 3, 21.20 mass % Polyisocyanate 3, and 0.20 mass % zinc-based catalyst were used, and the hydrophilic filler in Table 1 was replaced with 15.00 mass % sodium carboxymethyl cellulose (CMCNa). The expansion rate was 196%.

Example 16

A foam was prepared as in Example 5 except that 59.69 mass % Polyol 3, 20.11 mass % Polyisocyanate 3, and 0.20 mass % bismuth-based catalyst were used, and the hydrophilic filler in Table 1 was replaced with 20.00 mass % sodium carboxymethyl cellulose (dry CMCNa). The expansion rate was 120%. The dry CMCNa (water content: 0%) was prepared as follows: CMCNa was placed in a drying oven at 110° C. and the weight was measured every three hours or more until the weight no longer varied.

Example 17

A foam was prepared as in Example 5 except that 59.69 mass % Polyol 3, 20.11 mass % Polyisocyanate 3, and 0.20 mass % bismuth-based catalyst were used, and the hydrophilic filler in Table 1 was replaced with 20.00 mass % sodium carboxymethyl cellulose (CMCNa) having a higher water content. The expansion rate was 154%. The CMCNa having a higher water content was prepared by leaving CMCNa having a known weight and water content in a thermo-hygrostat at 40° C. and 75% Rh, where the water content was determined by the increased weight.

Example 18

A foam was prepared as in Example 5 except that 52.21 mass % Polyol 3, 17.59 mass % Polyisocyanate 3, and 0.20 mass % bismuth-based catalyst were used, and the hydrophilic filler in Table 1 was replaced with 30.00 mass % sodium carboxymethyl cellulose. The expansion rate was 182%.

Example 19

A foam was prepared as in Example 5 except that 53.43 mass % Polyol 3, 21.37 mass % Polyisocyanate 3, and 0.20 mass % bismuth-based catalyst were used, and the hydrophilic filler in Table 1 was replaced with 25.00 mass % sodium carboxymethyl cellulose (CMCNa). The expansion rate was 192%.

Example 20

A foam was prepared as in Example 5 except that 49.84 mass % Polyol 3, 19.94 mass % Polyisocyanate 3, and 0.20 mass % bismuth-based catalyst were used, and the hydrophilic filler in Table 1 was replaced with 30.00 mass % sodium carboxymethyl cellulose (CMCNa). The expansion rate was 195%.

Example 21

A foam was prepared as in Example 5 except that 49.20 mass % Polyol 2, 25.60 mass % Polyisocyanate 3, and 0.20 mass % bismuth-based catalyst were used, and the hydrophilic filler in Table 1 was replaced with 25.00 mass % sodium carboxymethyl cellulose (CMCNa). The expansion rate was 168%.

Example 22

A foam was prepared as in Example 5 except that 11.80 mass % Polyol 3, 63.00 mass % Polyisocyanate 2, and 0.20 mass % bismuth-based catalyst were used, and the hydrophilic filler in Table 1 was replaced with 25.00 mass % sodium carboxymethyl cellulose (CMCNa). The expansion rate was 268%.

Example 23

68.91 mass % Polyol 3 (equivalent: 2077.78), 20.89 mass % Polyisocyanate 3 (equivalent: 700.00), 0.20 mass % bismuth-based catalyst, and 10.00 mass % sodium carboxymethyl cellulose (20.9% CMCNa) containing 20.9 mass % water were mixed to prepare a mixture. The mixture was placed on a polyester releasing film. The top of the mixture was covered with another polyester releasing film to sandwich the mixture between the two polyester releasing films. The mixture with the two polyester releasing films was then heated in an oven at about 110° C. for one hour, and was further heated at about 40° C. for about three days to prepare a foam. The expansion rate was 210%.

Example 24

A foam was prepared as in Example 23 except that 59.69 mass % Polyol 3, 20.11 mass % Polyisocyanate 3, and 0.20 mass % bismuth-based catalyst were used, and CMCNa was replaced with 20.00 mass % sodium carboxymethyl cellulose (CMCNa) containing 0 mass % water. The expansion rate was 152%.

Example 252

A foam was prepared as in Example 23 except that 59.69 mass % Polyol 3, 20.11 mass % Polyisocyanate 3, 0.20 mass % bismuth-based catalyst, and 20.00 mass % CMCNa were used. The expansion rate was 253%.

Example 26

A foam was prepared as in Example 23 except that 59.69 mass % Polyol 3, 20.11 mass % Polyisocyanate 3, and 0.20 mass % a bismuth-based catalyst were used, and CMCNa was replaced with 20.00 mass % sodium carboxymethyl cellulose (CMCNa) containing 20.50 mass % water. The expansion rate was 313%. The CMCNa having a higher water content was prepared as in Example 17.

Example 27

A foam was prepared as in Example 23 except that 70.91 mass % Polyol 3, 23.89 mass % Polyisocyanate 3, 0.20 mass % bismuth-based catalyst, and 5.00 mass % CMCNa were used. The expansion rate was 141%.

Example 28

A foam was prepared as in Example 23 except that 67.51 mass % Polyol 3, 27.29 mass % Polyisocyanate 3, and 0.20 mass % bismuth-based catalyst were used, and CMCNa was replaced with 5.00 mass % sodium carboxymethyl cellulose (CMCNa). The expansion rate was 233%.

Example 29

A foam was prepared as in Example 23 except that 63.95 mass % Polyol 3, 23.85 mass % Polyisocyanate 3, and 0.20 mass % bismuth-based catalyst were used, and CMCNa was replaced with 10.00 mass % sodium carboxymethyl cellulose (CMCNa). The expansion rate was 293%.

Commercially available foam composites as Comparative Examples were used for comparison with the foam according to the present invention.

Comparative Example 1

Comparative Example 1 was a foam portion of a product (product name "HYDROSITE (registered trademark) AD Gentle" made by Smith & Nephew International S.A.). The calculated expansion rate was 1141%.

Comparative Example 2

Comparative Example 2 was a foam portion of a product (product name "Mepilex (registered trademark)" made by Molnlycke Health Care). The calculated expansion rate was 1002%.
(Evaluations and Results)
(Amount of Water Absorption)
Cylindrical test pieces having a thickness of 3 to 14 mm and a diameter of 30 mm were prepared from the foams according to Examples and the foam portions of the products according to Comparative Examples. Of each test piece, the thickness (height of the cylinder) and the weight (defined as Weight 1 of the test piece before water absorption) were measured. The circular test piece had a substantially flat surface. The test piece was immersed in saline at 37° C. The test piece was extracted every predetermined elapsed time. The water on the test piece was wiped off, and the weight (defined as Weight 1 of the test piece after water absorption) was measured. The amount of water absorption was calculated from Expression (1) where n is the circumference ratio.

[Expression 1]

Amount of water absorption (g/cm³)={(Weight 1 of test piece after water absorption)−(Weight 1 of test piece before water absorption)}/(1.5 cm×1.5 cm×π×thickness)     (1)

(Water Absorption Rate)
The water absorption rates (0 hr to 168 hr) of the foams prepared in Examples and Comparative Example were calculated from the following expression:

Water absorption rate (%)=[{(weight after immersion in saline)/(initial weight)}−1]×100

The calculated water absorption rates (0 hr to 168 hr) of the foams prepared in Examples and Comparative Examples are shown in Tables 2 to 4.
(Amount and Rate of Released Water)
Cylindrical test pieces having a thickness of 3 to 14 mm and a diameter of 30 mm were prepared from the foams according to Examples and the foam portions of the products according to Comparative Examples, and the weight of each test piece (defined as Weight 2 of the test piece before water absorption) was measured. The circular test piece had a substantially flat surface. The test piece was immersed in saline at 37° C. for seven days. The water on the test piece was wiped off, and the weight (defined as Weight 2 of the test piece after water absorption) was measured. The test sample was placed on a metal mesh, and a weight (500 g) was disposed on the sample. The sample was left for 10 seconds. The weight of the test sample (defined as Weight 2 of the test peace after water release) was then measured. The water release rate was calculated from Expression (2). The calculated water release rates of the foams prepared in Examples and Comparative Examples are shown in Tables 2 to 4.

[Expression 2]

Water release rate={(Weight 2 of test piece after water absorption)−(Test piece weight 2 after water release))/{(Test piece weight 2 after water absorption)−(Test piece weight 2 before water absorption)}     (2)

(Measurement of Sol Weight)
Cylindrical test pieces having a thickness of 3 to 14 mm and a diameter of 30 mm were prepared from the foams according to Examples and the foam portions of the products according to Comparative Examples, and the weight of each test piece was measured. The circular test piece had a substantially flat surface. The test piece was immersed in saline at 37° C. for seven days. After the test piece was sufficiently drained, the weight was measured. The substantially flat surface of the test piece was observed to find out a solated portion. The solated portion, if found out, was removed with a spatula. Although other surfaces than the flat surface also had solated portions, these solated portions were not removed. The sol weight was calculated from the difference in weight between the test piece after removal of the solated portion and the test piece before the removal of the solated portion.

In Examples 3 and 4, the test piece was also immersed in an aqueous 3% sodium citrate dihydrate solution instead of the saline to generate sol, and the sol weight was calculated by the same method. The calculated sol weights of the foams prepared in Examples and Comparative Example are shown in Tables 2 to 4.
(Measurement of Tackiness)
A method of evaluating (measuring) the tackiness of the foams prepared in Examples will now be described.

The tackiness was measured with a tackiness tester made by RHESCA Co., LTD., where the peak load was defined as tackiness.

Temperature: 23° C.

Humidity: 65%

Impression Speed: 30 mm/min

Press time: 20 sec

Test speed: 600 mm/min

Preload: 10 gf

The results of tackiness of the foams prepared in Examples are shown in Tables 2 to 4.
(Measurement of Thickness of Foam)
The thicknesses of the foams prepared in Examples were measured with a thickness gauge.

The thicknesses of the foams prepared in Examples and Comparative Examples are shown in Tables 2 to 4.
(Measurement of Water Content in Hydrophilic Polymer (hydrophilic Filler) Component)
The water content in the hydrophilic polymer or hydrophilic filler used in each of Examples 1, 2 and 5 to 29 was determined by loss on drying. The drying temperature was 110° C.

In Examples 1, 2 and 5 to 29, the water content in the hydrophilic polymer or hydrophilic filler and the water content in the composition for a foam (mixture before foaming) calculated from the corresponding water content in the hydrophilic polymer or hydrophilic filler are shown in Tables 2 to 4.

Figure 3:
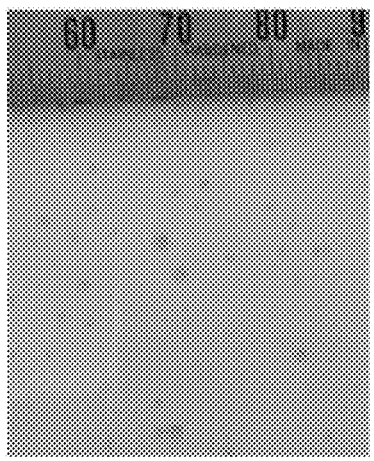
FIG. 3(a) illustrates the relation between the expansion rate of the foam according to an example of the present invention and the water content of the hydrophilic polymer.
FIG. 3(b) illustrates the relation between the expansion rate of the foam according to an example of the present invention and the water content of the hydrophilic polymer.
FIG. 3(c) illustrates the relation between the expansion rate of the foam according to an example of the present invention and the water content of the hydrophilic polymer.
Figure 3:
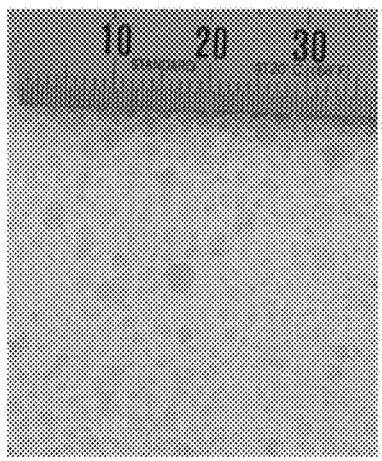
Figure 3:
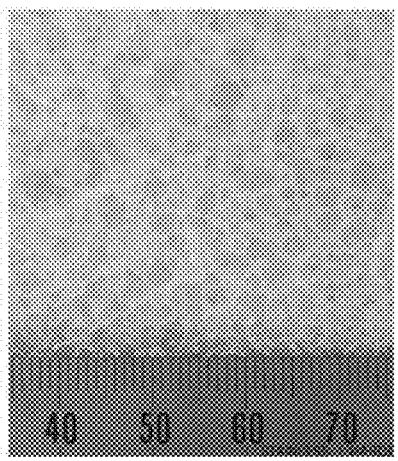

FIG. 3 illustrates the relation between the degree of foaming of the resulting foam and the water content of the hydrophilic polymer (sodium carboxymethyl cellulose (CMCNa)) used in Examples 24 to 26. Specifically, FIG. 3(a) illustrates a foam prepared in Example 24 using sodium carboxymethyl cellulose (CMCNa) having a water content of 0 mass %. FIG. 3(b) illustrates a foam prepared in Example 25 using sodium carboxymethyl cellulose (CMCNa) having a water content of 14.00 mass %. FIG. 3(c) illustrates a foam prepared in Example 26 using sodium carboxymethyl cellulose (CMCNa) having a water content of 20.50 mass %. FIGS. 3(a) to 3(c) evidently demonstrate that a higher water content in the hydrophilic polymer (sodium carboxymethyl cellulose (CMCNa)) resulted in a higher expansion level (expansion rate). As described above, the foams shown in FIGS. 3(a) to (c) are each provided with releasing films on two main surface (two outer surfaces) of the foam to prevent the leakage of air.

TABLE 2

|  | Example 1 | Example 2 | Example 3 | Example 4 | Example 5 | Example 6 | Example 7 | Example 8 | Example 9 | Example 10 |
|---|---|---|---|---|---|---|---|---|---|---|
| Polyol 1 (mass) % | 66.9% | 69.2% | | | | | | | | |
| Polyisocyanate 1 (mass) % | 11.1% | 13.8% | | | | | | | | |
| Polyol 2 (mass) % | | | 29.1% | 64.9% | 61.8% | 64.0% | 62.6% | 61.40% | 61.40% | 60.08% |
| Polyisocyanate 2 (mass) % | | | 9.4% | 8.7% | 12.4% | 8.0% | 10.4% | 12.30% | 12.30% | 14.72% |
| Polyol 3 (mass) % | | | | | | | | | | |
| Polyisocyanate 3 (mass) % | | | | | | | | | | |
| Bismuth-based catalyst (mass) % | | | | | | | | | 0.20% | |
| Zinc-based catalyst (mass) % | | | | | | | | | | |
| Metal carbonate catalyst (zinc) (mass) % | 2.0% | 2.0% | 1.5% | 1.5% | 0.9% | 3.0% | 2.0% | 1.50% | 1.50% | |
| Amount of hydrophilic filler component (mass) % | 20.0% | 15.0% | 50.0% | 25.0% | 25.0% | 25.0% | 25.0% | 25.00% | 25.00% | 25.00% |
| Description of hydrophilic filler | (CMCNa, pectin, etc.) | | (AlgCa) | (AlgCa) | (CMCNa, pectin, etc.) | | | | Dried product | CMCNa |
| NCO/OH | 0.927 | 0.773 | 3.257 | 0.652 | 0.980 | 0.611 | 0.814 | 0.979 | 0.979 | 1.197 |
| Water content in hydrophilic polymer component (mass) % | 11.60% | 11.60% | — | — | 11.60% | 11.60% | 11.60% | 11.60% | 0.00% | 14.00% |
| Overall water content (mass) % | 2.32% | 1.74% | — | — | 2.90% | 2.90% | 2.90% | 2.90% | 0.00% | 3.50% |
| Thickness mm | 3.80 mm | 5.40 mm | 14.00 mm | 3.30 mm | 6.29 mm | 3.03 mm | 6.06 mm | 7.40 mm | 2.70 mm | 3.92 mm |
| Expansion rate % | 183% | 281% | 441% | 166% | 422% | 134% | 253% | 314% | 112% | 206% |
| Tackiness N | — | — | — | — | 0.050N | 0.424N | 0.087N | — | — | 0.013N |
| Sol weight g | 0.134 g | 0.151 g | 0.237 g | 0.114 g | 0.114 g | 0.126 g | 0.225 g | — | — | 0.212 g |
| Water release rate % | 1.4% | 3.1% | 13.3% | 1.4% | 8.5% | 0.1% | 0.3% | — | — | 0.3% |
| Water absorption rate (0 hr) | 0% | 0% | 0% | 0% | 0% | 0% | 0% | — | — | 0% |
| 6 hr | 103% | 160% | — | — | 424% | 130% | 391% | — | — | 205% |
| 24 hr | 184% | 237% | 317% | 92% | 436% | 199% | 424% | — | — | 300% |
| 48 hr | 193% | 251% | 413% | 149% | 442% | 240% | 439% | — | — | 316% |
| 168 hr | 241% | 272% | — | — | 434% | 306% | 434% | — | — | 324% |
| Wound dressing | B | B | B | B | B | B | B | B | B | B |
| Skin protector | — | — | | — | — | — | — | — | — | — |
| Hemostatic material | — | — | A | B | — | — | — | — | — | — |
| Tape (for fixation/protection) | — | — | — | — | — | — | — | — | — | — |

TABLE 3

|  | Example 11 | Example 12 | Example 13 | Example 14 | Example 15 | Example 16 | Example 17 | Example 18 | Example 19 | Example 20 | Example 21 | Example 22 |
|---|---|---|---|---|---|---|---|---|---|---|---|---|
| Polyol 1 (mass) % | | | | | | | | | | | | |
| Polyisocyanate 1 (mass) % | | | | | | | | | | | | |
| Polyol 2 (mass) % | | | | | | | | | | | 49.20% | |
| Polyisocyanate 2 (mass) % | | | | | | | | | | | | 63.00% |
| Polyol 3 (mass) % | 70.54% | 72.66% | 56.48% | 70.73% | 63.60% | 59.69% | 59.69% | 52.21% | 53.43% | 49.84% | | 11.80% |
| Polyisocyanate 3 (mass) % | 14.26% | 17.14% | 13.32% | 19.07% | 21.20% | 20.11% | 20.11% | 17.59% | 21.37% | 19.94% | 25.60% | |
| Bismuth-based catalyst (mass) % | 0.20% | 0.20% | 0.20% | 0.20% | | 0.20% | 0.20% | 0.20% | 0.20% | 0.20% | 0.20% | 0.20% |
| Zinc-based catalyst (mass) % | | | | | 0.20% | | | | | | | |
| Metal carbonate catalyst (zinc) (mass) % | | | | | | | | | | | | |
| Amount of hydrophilic filler component (mass) % | 15.00% | 10.00% | 30.00% | 10.00% | 15.00% | 20.00% | 20.00% | 30.00% | 25.00% | 30.00% | 25.00% | 25.00% |
| Description of hydrophilic filler | CMCNa | CMCNa | CMCNa | CMCNa | CMCNa | dried CMCNa | CMCNa higher water content | CMCNa | CMCNa | CMCNa | CMCNa | CMCNa |
| NCO/OH | 0.600 | 0.700 | 0.700 | 0.800 | 0.989 | 1.000 | 1.000 | 1.000 | 1.187 | 1.188 | 1.191 | 33.807 |
| Water content in hydrophilic polymer component (mass) % | 14.00% | 14.00% | 14.00% | 14.00% | 14.00% | 0.00% | 20.50% | 14.00% | 14.00% | 14.00% | 14.00% | 14.00% |
| Overall water content (mass) % | 2.10% | 1.40% | 4.20% | 1.40% | 2.10% | 0.00% | 4.10% | 4.20% | 3.50% | 4.20% | 3.50% | 3.50% |

TABLE 3-continued

| | Example 11 | Example 12 | Example 13 | Example 14 | Example 15 | Example 16 | Example 17 | Example 18 | Example 19 | Example 20 | Example 21 | Example 22 |
|---|---|---|---|---|---|---|---|---|---|---|---|---|
| Thickness mm | 2.13 mm | 1.75 mm | 3.50 mm | 2.10 mm | 3.27 mm | 3.93 mm | 2.35 mm | 3.70 mm | 3.77 mm | 4.27 mm | 3.40 mm | 4.50 mm |
| Expansion rate % | 119% | 102% | 154% | 125% | 196% | 120% | 154% | 182% | 192% | 195% | 168% | 268% |
| Tackiness N | 1.807N | 2.174N | 0.637N | 1.553N | 0.383N | 0.041N | 0.529N | 0.346N | 0.174N | 0.137N | 0.050N | 0.054N |
| Sol weight g | — | — | — | 0.297 g | 0.162 g | 0.088 g | 0.368 g | — | 0.418 g | 0.250 g | 0.148 g | 0.000 g |
| Water release rate % | — | — | — | 4.4% | 0.7% | 0.7% | 4.3% | — | 0.6% | 1.5% | 0.05% | 0.2% |
| Water absorption rate (0 hr) | 0% | 0% | 0% | 0% | 0% | 0% | 0% | 0% | 0% | 0% | 0% | 0% |
| 6 hr | 237% | 142% | 436% | 64% | 168% | 43% | 202% | 351% | 157% | 252% | 155% | 126% |
| 24 hr | 335% | 347% | 776% | 141% | 253% | 81% | 368% | 642% | 328% | 543% | 245% | 200% |
| 48 hr | — | 349% | — | 171% | 266% | 111% | 395% | 813% | 406% | 659% | 272% | 223% |
| 168 hr | — | — | — | 214% | 267% | 169% | 436% | — | 541% | 740% | 309% | 204% |
| Wound dressing | B | C | C | B | B | B | A | B | B | B | B | B |
| Skin protector | B | C | — | A | — | — | — | — | — | — | — | — |
| Hemostatic material | — | — | — | — | — | — | — | — | — | — | — | — |
| Tape (for fixation/protection) | B | C | — | B | — | — | — | — | — | — | — | — |

TABLE 4

| | Example 23 | Example 24 | Example 25 | Example 26 | Example 27 | Example 28 | Example 29 | Comparative Example 1 | Comparative Example 2 |
|---|---|---|---|---|---|---|---|---|---|
| Polyol 1 (mass) % | | | | | | | | | |
| Polyisocyanate 1 (mass) % | | | | | | | | | |
| Polyol 2 (mass) % | | | | | | | | | |
| Polyisocyanate 2 (mass) % | | | | | | | | | |
| Polyol 3 (mass) % | 68.91% | 59.69% | 59.69% | 59.69% | 70.91% | 67.51% | 63.95% | | |
| Polyisocyanate 3 (mass) % | 20.89% | 20.11% | 20.11% | 20.11% | 23.89% | 27.29% | 25.85% | | |
| Bismuth-based catalyst (mass) % | 0.20% | 0.20% | 0.20% | 0.20% | 0.20% | 0.20% | 0.20% | | |
| Zinc-based catalyst (mass) % | | | | | | | | | |
| Metal carbonate catalyst (zinc) (mass) % | | | | | | | | | |
| Amount of hydrophilic filler component (mass) % | 10.00% | 20.00% | 20.00% | 20.00% | 5.00% | 5.00% | 10.00% | | |
| Description of hydrophilic filler | CMCNa | CMCNa dried | CMCNa | CMCNa Higher water content | CMCNa | CMCNa | CMCNa | | |
| NCO/OH | 0.900 | 1.000 | 1.000 | 1.000 | 1.000 | 1.200 | 1.200 | | |
| Water content in hydrophilic polymer component (mass) % | 14.00% | 0.00% | 14.00% | 20.50% | 14.00% | 14.00% | 14.00% | | |
| Overall water content (mass) % | 2.09% | 0.00% | 2.80% | 4.10% | 0.70% | 0.70% | 1.40% | | |
| Thickness mm | 2.35 mm | 2.65 mm | 3.10 mm | 3.68 mm | 2.10 mm | 3.33 mm | 3.90 mm | 4.10 mm | 4.60 mm |
| Expansion rate % | 210% | 152% | 253% | 313% | 141% | 233% | 293% | 1141% | 1002% |
| Tackiness N | 1.050N | 0.761N | 0.279N | 0.158N | 0.670N | 0.612N | 0.833N | No tackiness | No tackiness |
| Sol weight g | — | 0.167 g | — | 0.000 g | 0.226 g | 0.222 g | 0.150 g | Not solated | Not solated |
| Water release rate % | — | 0.5% | — | 3.0% | 2.6% | 3.3% | 2.4% | 49.1% | 43.90% |
| Water absorption rate (0 hr) | 0% | 0% | 0% | 0% | 0% | 0% | 0% | 0% | 0% |
| 6 hr | 278% | 128% | — | 424% | 50% | 69% | 236% | 1654% | 1419% |
| 24 hr | 310% | 268% | — | 435% | 71% | 99% | 251% | 1637% | 1421% |
| 48 hr | — | 355% | — | 391% | 84% | 122% | 259% | 1682% | 1440% |
| 168 hr | — | 471% | — | 350% | 108% | 140% | 254% | 1740% | 1442% |
| Wound dressing | C | B | C | B | B | B | B | | |
| Skin protector | C | B | — | — | — | — | — | | |
| Hemostatic material | — | — | — | — | — | — | — | | |
| Tape (for fixation/protection) | C | A | — | — | B | B | B | | |

Tables 2 to 4 demonstrate that the foams in Examples have appropriate water absorption rates, and have water release rates lower than those in Comparative Examples. For example, if foam composites including the foams according to Examples are applied to surfaces of wounds having large amounts of exudate, these foams can absorb the exudate. Even if any pressure is applied to the foam composites, most of the absorbed exudate does not return to the surfaces of wounds. Furthermore, the foams according to Examples absorb water and solate. As described above, the sol present on the surfaces of wounds is expected to keep a wet environment of the surfaces of wounds to promote the cure of the wounds and to provide pain relief.

(Test on Dry Tackiness and Tackiness After Water Absorption)
<Procedure>

The dry tackiness and tackiness after water absorption was evaluated in accordance with the following procedure.

1. A test piece or sample was selected that had a tackiness of 0.4 N or more and was nondisintegrable during water absorption.

2. To avoid elongation of the sample, a packing tape was applied to the rear surface of the sample. The sample was cut into a width of 15 mm, and was bonded onto a slide glass such that the length of the adhesive portion was 35 mm or more.

3. A dry (before water absorption) sample was prepared by leaving the sample at 37° C. for 2.5 hours. The sample after water absorption was prepared by immersing the sample in saline at 37° C. for 2.5 hours and wiping off circumjacent water from the sample.

4. The dry (before water absorption) sample and the sample after water absorption were left to stand at 23° C. and 65% RH or more. After these samples were exposed to room temperature, the samples were subjected to a 180° peel test at a peeling rate of 300 mm/min. In each of the sample, the average of the peel forces from 30 to 50 mm was defined as tackiness.

The tackiness retention rate was calculated from the following expression:

Tackiness retention rate=(tackiness of sample after water absorption)/(tackiness of dry (before water absorption) sample)

The samples used were the foams prepared in Examples 6, 14, 17, 24 and 27 to 28. The tackiness retention rate is shown in Table 5.

TABLE 5

| Sample name | Dried After 2.5 hr | 2.5 hr, 37° C. After immersion in saline | Tackiness retention rate (tackiness of sample after water absorption)/ (tackiness of dry (before water absorption) sample) |
|---|---|---|---|
| HS (Comparative Example) | 0.52N | 0.00N | 0% |
| Example 17 | 3.51N | 3.48N | 99% |
| Example 14 | 6.01N | 3.28N | 55% |
| Example 24 | 4.37N | 3.64N | 83% |
| Example 27 | 13.69N | 5.18N | 38% |
| Example 28 | 5.56N | 0.11N | 2% |
| Example 6 | 0.99N | 2.37N | 240% |

Table 5 evidently demonstrates that the foams prepared in Examples 6, 14, 17, 24 and 27 to 28 had satisfactory tackiness retention rates.

While the foams of the present invention can be used in any medical application, the foams are suitable for applications to wound dressings, skin protectors, hemostatic materials, and tapes (fixation/protection). Tables 2 to 4 show which application is suitable for the foams prepared in Examples 1 to 29 among wound dressings, skin protectors, hemostatic materials, and skin tapes (fixation/protection). The evaluation of applications was performed according to the following criteria:

(Criteria for Evaluation of Applications)
A . . . perfectly suitable
B . . . eminently suitable
C . . . suitable The aspects of the present invention are as follows:

[1] A foam prepared by a foam reaction of a mixture comprising:
   at least one polyol;
   a compound having at least one isocyanate group; and
   a hydrophilic polymer.
[2] The foam according to Aspect [1],
   wherein surfaces of the foam solate after water absorption.
[3] The foam according to Aspect [1] or [2],
   wherein the foam has a water release rate of 0 to 30%.
[4] The foam according to any one of Aspects [1] to [3],
   wherein the hydrophilic polymer contains 10 mass % or more water.
[5] The foam according to any one of Aspects [1] to [4],
   wherein the foam has an expansion rate of 110% to 500%.
[6] The foam according to any one of Aspects [1] to [5],
   wherein the surfaces of the foam have tackiness before and/or after the water absorption.
[7] The foam according to any one of Aspects [1] to [6],
   wherein the foam has a water absorption rate of 40% or more after immersion in water for six hours.
[8] The foam according to any one of Aspects [1] to [7],
   wherein the mixture comprises
   25 to 80 mass % polyol;
   5 to 30 mass % compound having at least one isocyanate group; and
   5 to 50 mass % hydrophilic polymer.
[9] The foam according to any one of Aspects [1] to [8],
   further comprising a bioactive substance such as ceramide.
[10] The foam according to any one of Aspects [1] to [9],
   wherein the foam has a thickness of 1.5 mm or more.
[11] The foam according to any one of Aspects [1] to [10],
   wherein the polyol has an OH equivalent of 1000 or more, and polyisocyanate has an NCO equivalent of 100 or more.
[12] A composition for a foam comprising:
   at least one polyol;
   a compound having at least one isocyanate group; and
   a hydrophilic polymer.
[13] The composition for a foam according to Aspect [12],
   wherein a content of the polyol is 25 to 80 mass %,
   a content of the compound having at least one isocyanate group is 5 to 30 mass %, and
   a content of the hydrophilic polymer is 5 to 50 mass %.
[14] The composition for a foam according to Aspect [12] or [13],
   wherein the hydrophilic polymer contains 10 mass % or more water.
[15] The composition for a foam according to any one of Aspects [12] to [14],
   wherein the polyol has an OH equivalent of 1000 or more, and polyisocyanate has an NCO equivalent of 100 or more.
[16] A wound dressing, comprising the foam according to any one of Aspects [1] to [11].
[17] A skin protector for ostomy appliances, comprising the foam according to any one of Aspects [1] to [11].
[18] A skin tape, comprising the foam according to any one of Aspects [1] to [11].
[19] A hemostatic material comprising the foam according to any one of Aspects [1] to [11].

REFERENCE SIGNS LIST

1 . . . foam composite, 10 . . . substrate, 20 . . . foam

The invention claimed is:

1. A foam prepared by foaming and reacting a mixture comprising:
    at least one polyol;
    a compound having at least one isocyanate group; and
    a hydrophilic polymer, wherein the hydrophilic polymer contains at least calcium alginate and 10 to 20.5 mass % water, wherein:
    the foam is generated due to the reaction of water contained in the hydrophilic polymer,
    the foam does not contain any surfactant, and
    the mixture comprises:
        25 to 80 mass % of the at least one polyol;
        5 to 30 mass % of the compound having at least one isocyanate group; and
        5 to 50 mass % of the hydrophilic polymer.
2. The foam according to claim 1,
    wherein surfaces of the foam solate after water absorption.
3. The foam according to claim 1,
    wherein the foam has a water release rate of 0 to 30% measured in weight percentage.
4. The foam according to claim 1,
    wherein the foam has an expansion rate of 140% to 500% measured in volume percentage.
5. The foam according to claim 1,
    wherein the surfaces of the foam have tackiness before and/or after water absorption.
6. The foam according to claim 1,
    wherein the foam has a water absorption rate of 40% or more measured in weight percentage after immersion in water for six hours.
7. The foam according to claim 1, further comprising a bioactive substance.
8. The foam according to claim 1,
    wherein the foam has a thickness of 1.5 mm or more.
9. The foam according to claim 1,
    wherein the at least one polyol has 1000 or more in gram equivalents for OH, and the compound having at least one isocyanate group has 100 or more in gram equivalents for NCO.
10. A composition for a foam comprising:
    at least one polyol;
    a compound having at least one isocyanate group; and
    a hydrophilic polymer, wherein the hydrophilic polymer contains at least calcium alginate and 10 to 20.5 mass % water, wherein:
    the foam is generated due to the reaction of water contained in the hydrophilic polymer,
    the composition does not contain any surfactant, and
        a content of the at least one polyol is 25 to 80 mass %;
        a content of the compound having at least one isocyanate group is 5 to 30 mass %; and
        a content of hydrophilic polymer is 5 to 50 mass %.
11. The composition for a foam according to claim 10,
    wherein the at least one polyol has 1000 or more in gram equivalents for OH, and the compound having at least one isocyanate group has 100 or more in gram equivalents for NCO.
12. A wound dressing, comprising the foam according to claim 1.
13. A skin protector for ostomy appliances, comprising the foam according to claim 1.
14. A skin tape, comprising the foam according to claim 1.
15. A hemostatic material, comprising the foam according to claim 1.
16. The foam according to claim 1, wherein a thickness of the foam is 2.35 mm or more.

* * * * *